US006584830B2

(12) United States Patent
Long

(10) Patent No.: US 6,584,830 B2
(45) Date of Patent: Jul. 1, 2003

(54) VISCOSITY MEASURING APPARATUS

(75) Inventor: Michael Long, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 52 days.

(21) Appl. No.: 09/880,383

(22) Filed: Jun. 13, 2001

(65) Prior Publication Data

US 2003/0010096 A1 Jan. 16, 2003

(51) Int. Cl.$^7$ .............................. G01N 11/08; G02F 1/46
(52) U.S. Cl. .................... 73/54.09; 73/54.06; 73/54.14; 73/861.66
(58) Field of Search ............................. 73/54.04, 54.05, 73/54.06, 54.09, 54.11, 54.14, 861.65, 861.66

(56) References Cited

U.S. PATENT DOCUMENTS 2,771,770 A * 11/1956 Bouman .................... 73/54.09
4,320,665 A * 3/1982 Cain ........................ 73/861.04
4,750,351 A * 6/1988 Ball .......................... 73/54.04
4,957,007 A * 9/1990 Gray ............................ 73/182

FOREIGN PATENT DOCUMENTS

JP                62-211542        * 9/1987

* cited by examiner

Primary Examiner—Hezron Williams
Assistant Examiner—Michael Cygan
(74) Attorney, Agent, or Firm—Raymond L. Owens

(57) ABSTRACT

Apparatus for measuring the viscosity of a Newtonian fluid, includes a tubular housing which defines an internal cavity; a fluid restriction structure disposed in a first portion of the cavity; and a pressure measuring device disposed to measure the differential pressure in the cavity of the fluid which has flowed through the fluid restriction structure. The apparatus further includes a device for applying pressure to the fluid upstream from the fluid restriction structure to cause the fluid to flow through the fluid restriction structure so that the pressure measuring device measures the pressure differential which is inversely proportional to the fluid viscosity squared.

4 Claims, 5 Drawing Sheets

VISCOSITY MEASURING APPARATUS

FIELD OF THE INVENTION

The present invention relates to apparatus for measuring the viscosity of fluids by determining pressure differentials.

BACKGROUND OF THE INVENTION

The measurement of viscosity is fundamental to a multitude of industrial processes and many types of apparatus have been developed. The Saybolt viscometer measures the time rate of flow for a fixed volume of fluid to flow through a fine capillary tube. The viscosity is linearly proportional to the drain time according to Equation (1).

$$\mu = \left(\frac{\pi D^4 h_L \gamma}{128 V_L L}\right) t \quad (1)$$

where

D is the tube diameter
$h_L$ is the fluid head loss
$\gamma$ is the fluid specific weight
$V_L$ is fluid volume exiting the tube in time t
L is the tube length
t is time Another method measures the time for a given mass, usually a sphere, to fall through a fixed dimension, usually stagnant, column of fluid. Viscosity is linearly proportional to the measured fall time according to Equation (2).
for $D/D_T < \frac{1}{3}$ $$\mu = \left[\frac{D^2(\gamma_S - \gamma)}{18L\left(1 + \frac{9D}{4D_T} + \left(\frac{9D}{4D_T}\right)^2\right)}\right] t \quad (2)$$

where

D is the sphere diameter
$\gamma_S$ is the sphere specific weight
$\gamma$ is the fluid specific weight
$D_T$ is the tube diameter
t is time A variation of this method measures the time for a bubble to rise through a column of fluid.

A third method, known as the Brookfield viscometer measures the force or torque to overcome viscous shear forces between fixed and moving surfaces submerged in a fluid. These surfaces usually take the form of concentric cylinders. With this method, viscosity is linearly proportional to the measured force or torque according to Equation (3).

$$\mu = \frac{FS}{AV} \quad (3)$$

where

F is the measured force
S is the fluid thickness
A is the wetted area
V is the differential velocity The aforementioned methods of measuring viscosity are not well adapted to continuous measurement of process fluids as they require batch processing of fixed fluid volumes or involve stagnant columns of fluid. In response, another class of viscometer using a flow-through geometry was introduced where the pressure drop through a friction tube is measured when a liquid is pumped through it at a constant flow rate, Q. From the Poiseuille law shown in Equation (4), the viscosity, $\mu$ is seen to be linearly proportional to the pressure differential, $P_d$.

$$\mu = \frac{\pi P_d \gamma D^4}{128 QL} \quad (4)$$

Stagnant or trapped fluid volumes increase the measurement error in a continuous system where the bulk fluid viscosity is to be measured and controlled. The trapped fluid properties are not representative of changing bulk fluid properties because they do not change at the same rate as the bulk fluid in response to a control signal. In general, the bulk fluid properties slowly diffuse into the trapped fluid volume, presenting a significant time lag between a control signal and the response.

SUMMARY OF THE INVENTION

It is an object of the present invention to provide an apparatus, which can effectively measure viscosity and does not use the linearity techniques employed by the prior art.

This object is achieved in an apparatus for measuring the viscosity of a Newtonian fluid, comprising:

(a) a tubular housing which defines an internal cavity;
(b) a fluid restriction structure disposed in a first portion of the cavity;
(c) a pressure measuring device disposed to measure the differential pressure in the cavity of the fluid which has flowed through the fluid restriction structure; and
(d) a device for applying pressure to the fluid upstream from the fluid restriction structure to cause the fluid to flow through the fluid restriction structure so that the pressure measuring device measures the pressure differential which is inversely proportional to the fluid viscosity squared.

It has been determined that viscosity measuring apparatus can make use of a continuous flow design where fluid under constant pressure flows through the apparatus at a flow velocity that is inversely proportional to the fluid viscosity. The differential pressure measured across upstream and downstream pointing Pitot tubes in the viscometer is proportional to the square of the flow velocity and is therefore inversely proportional to the fluid viscosity squared.

An important feature of the present invention is that the accuracy of viscosity measurements can be significantly improved. Moreover, measurements can be made using the same apparatus more frequently than in the prior art and in fact continuously, without adversely affecting the measurements.

DETAILED DESCRIPTION OF THE INVENTION

Figure 1A:
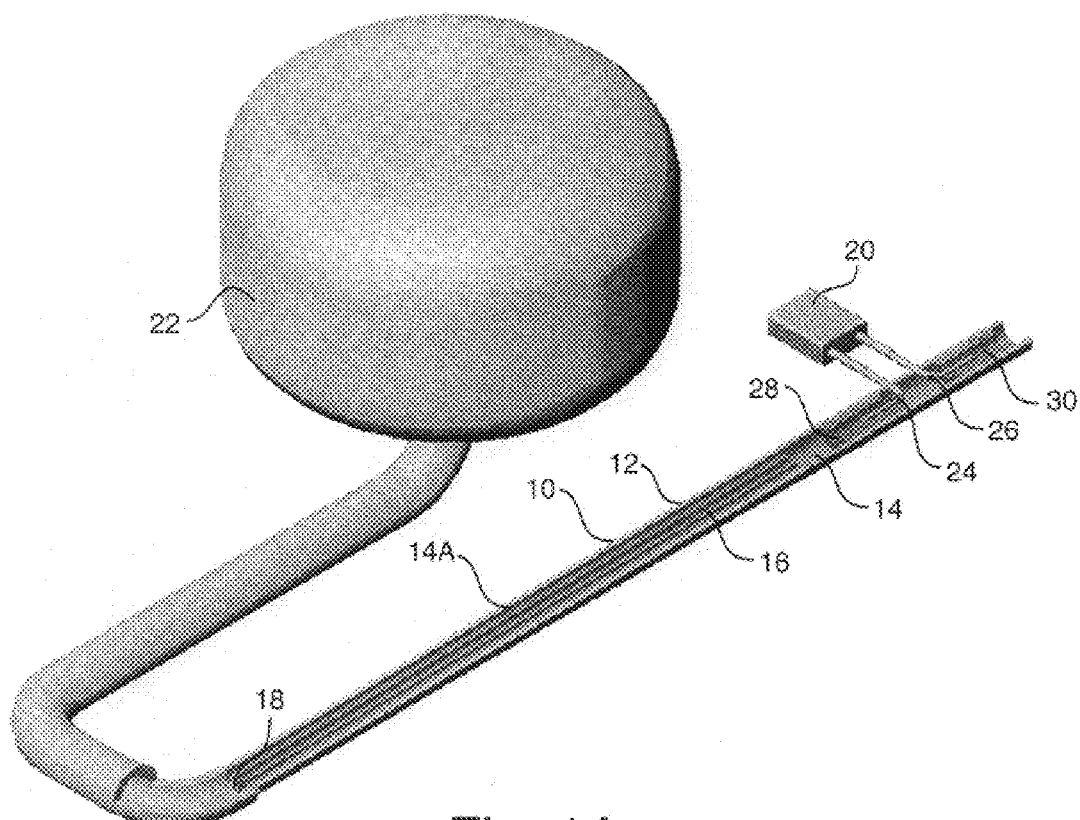
FIG. 1A is a broken away pictorial partially shown in schematic of one embodiment in accordance with the present invention.
Figure 1B:
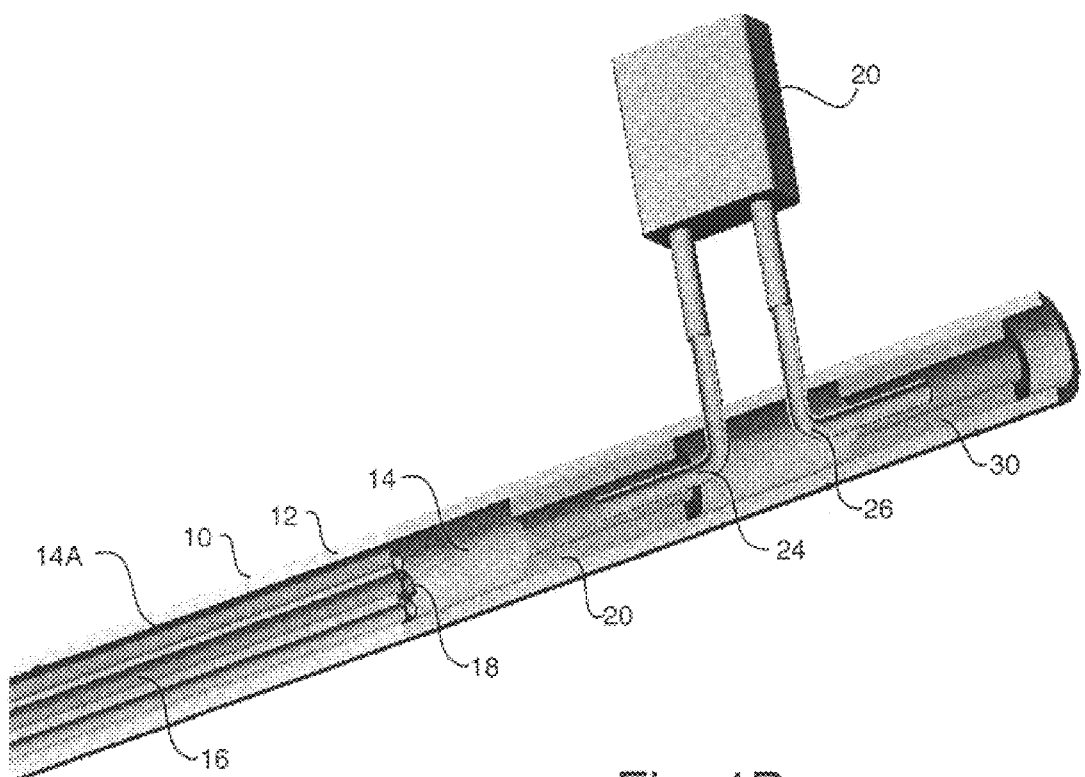
FIG. 1B is a magnified view of a portion of FIG. 1A.

A schematic pictorial of the apparatus for measuring viscosity is shown in FIG. 1A with a magnified view of a portion of the apparatus shown in FIG. 1B. The apparatus 10 includes a tubular housing 12, which defines an internal cavity 14. The term "tubular" is not used in any strictive sense and although the internal cavity 14 is shown as having a uniform circular cross-section it can have a number of different configurations. In accordance with the present invention a fluid restricting structure 16 is disposed in a first portion 14a of the internal cavity 14. The fluid restricting structure 16 in the FIG. 1A embodiment is provided by a plurality of capillary restrictive tubes 18.

Figure 2:
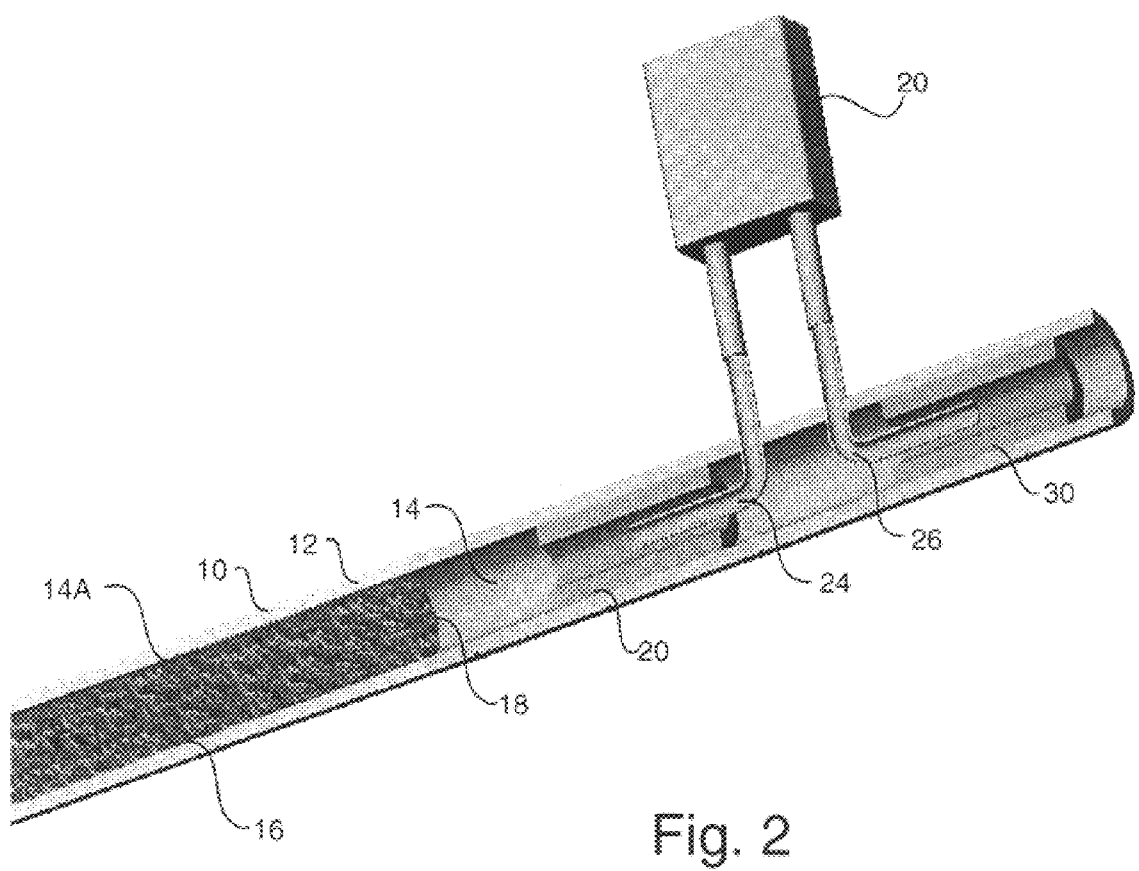
FIG. 2 is another broken away pictorial similar to FIG. 1B except having a different fluid flow restricting structure.

In the embodiment of FIG. 2 a porous material such as a sintered stainless steel or alumina ceramic material provides a plurality of passageways 18a. These passageways 18a typically have a diameter of about 20 microns so for clarity of illustration these passageways 18a have been exaggerated in diameter. The average fluid velocity, V, and flow rate, Q, through the restricting structure varies inversely with viscosity, nominally following the Poiseuille law, shown in Equation 5.

$$V = \frac{h_l \gamma R_h^2}{2\mu L} \quad (5)$$

where $h_l$ is the pressure drop across the restrictor $\gamma$ is the specific gravity of the fluid $R_h$ is the hydraulic radius $\mu$ is the fluid viscosity L is the length of the restrictor The second element of the apparatus includes a device known as a Pitotmeter, that infers the flow rate, Q, from the differential pressure across upstream and downstream oriented hollow tubes, known as Pitot tubes 24, 26 disposed in cavity 14. Flow area reducers 28, 30 placed near the ends of the Pitot tubes 24, 26 locally increase the fluid velocity and thereby increase the differential fluid pressure.

For the upstream and downstream pointing Pitot tubes shown in FIG. 1B and FIG. 2, the local flow velocity, u, is determined from the differential pressure by Equation (6)

$$u = \sqrt{2\left(\frac{P_s}{\rho} - \frac{P_d}{\rho}\right)} \quad (6)$$

where $p_s$ is the stagnation pressure measured at the upstream Pitot tube $p_d$ is the pressure measured at the downstream Pitot tube $\rho$ is the fluid density ($\gamma/g$)

u is the local fluid velocity in the undisturbed flow

Substituting the maximum velocity $u_m = 2V$ in laminar flow for u, and combining with Equation (5) yields Equation (7), where k is a constant for the system. This equation shows that the measured pressure differential, $p_s - p_d$, is inversely proportional to the viscosity squared.

$$p_s - p_d = \frac{\rho^3 R_h^4 g^2 h_L^2}{2\mu^2 L^2} = \frac{k}{\mu^2} \quad (7)$$

A pressure measuring device 20 is disposed to measure the differential pressure across the Pitotmeter structure in the portion of the internal cavity 14 following the fluid restricting structure 16. The output signal from pressure measuring device 20 varies as a system constant, k, over the viscosity squared.

A device 22 for applying pressure to the fluid upstream from the fluid restricting structure 16 to cause the fluid to flow through the fluid restricting structure 16 so that the pressure measuring device 20 measures the pressure differential that is inversely proportional to the fluid viscosity squared.

None of the prior art located to date suggests that different restrictor geometries would show significant, constant pressure drop, flow rate differences in response to a given viscosity difference in a pure fluid. Similarly, the Poiseuille law in laminar flow would predict that two restrictors having equal flow rates, $Q_1$, for a fluid of given specific gravity and pressure drop, $h_1$, at one viscosity, $\mu_1$, should have equal flow rates, $Q_2$, for the same fluid at a second viscosity, $\mu_2$. That the Poiseuille law is not followed in the tested restrictors is an unexpected result.

Figure 3:
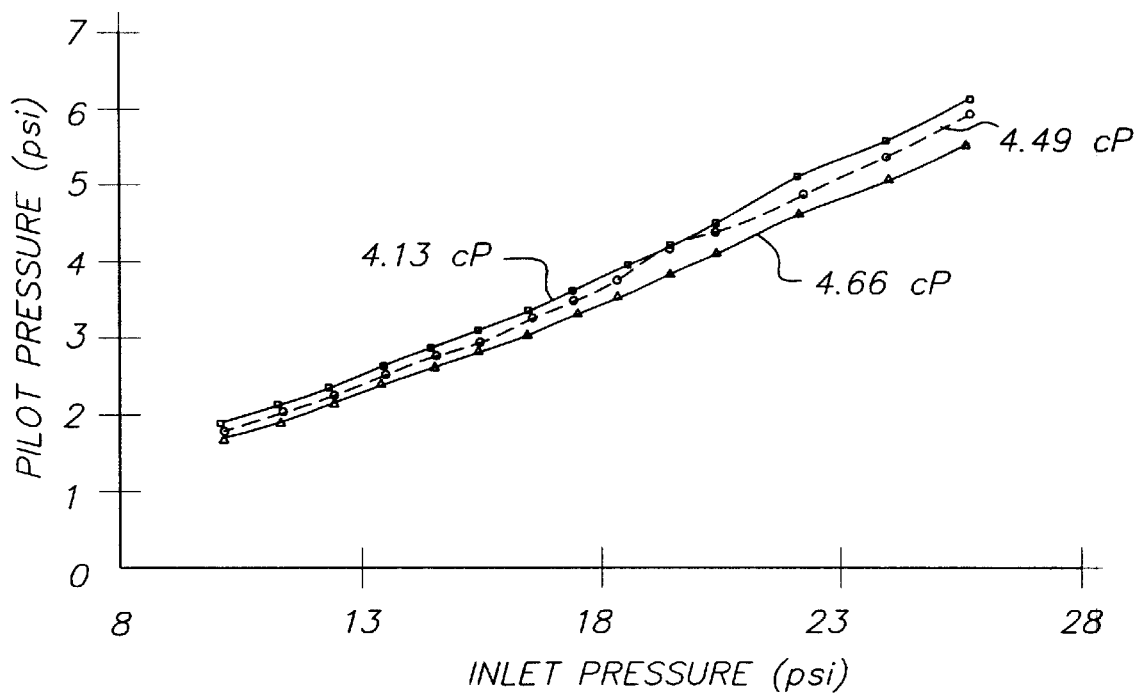
FIG. 3 is a graph showing Pitot pressure versus inlet pressure for a particularly capillary tube apparatus.

FIG. 3 shows a plot of differential Pitot pressure versus supply pressure for solutions of 38, 40 and 42% dipropylene glycol methyl ether in water at 22° C. having viscosities of 4.13, 4.49 and 4.66 cP, respectively. Data is for an embodiment using a 190 mm long, 8 capillary tube restrictor bundle.

Figure 4:
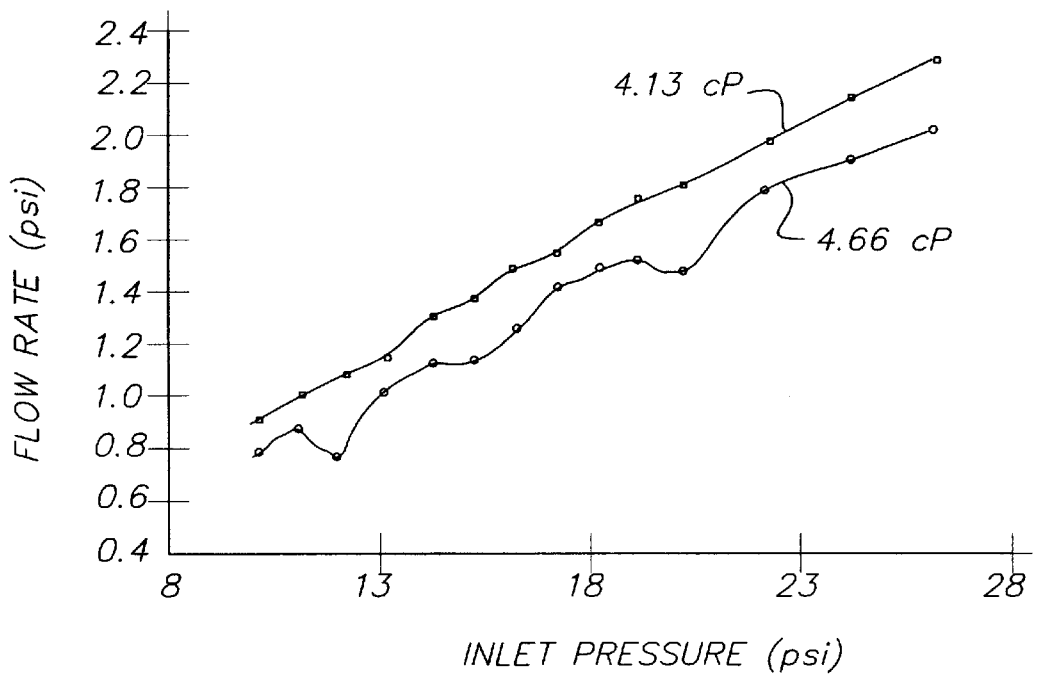
FIG. 4 is a graph of flow rate versus inlet pressure for the capillary tube apparatus of FIG. 3.

FIG. 4 is a graph of flow rate versus driving pressure for the preferred capillary tube apparatus for solutions of 38 and 42% dipropylene glycol methyl ether in water having viscosities of 4.13 and 4.66 cP, respectively. A flow rate difference of 200 ml/s was obtained for a driving pressure of 23 psi. This data was obtained with a 190 mm long, 8 capillary tube restrictor bundle. The flow rate differentiation as a function of viscosity is not as great as was measured for the porous ceramic restrictor, but the propensity for fouling and clogging is substantially smaller for the capillary tube geometry as compared to the porous material configuration.

Figure 5:
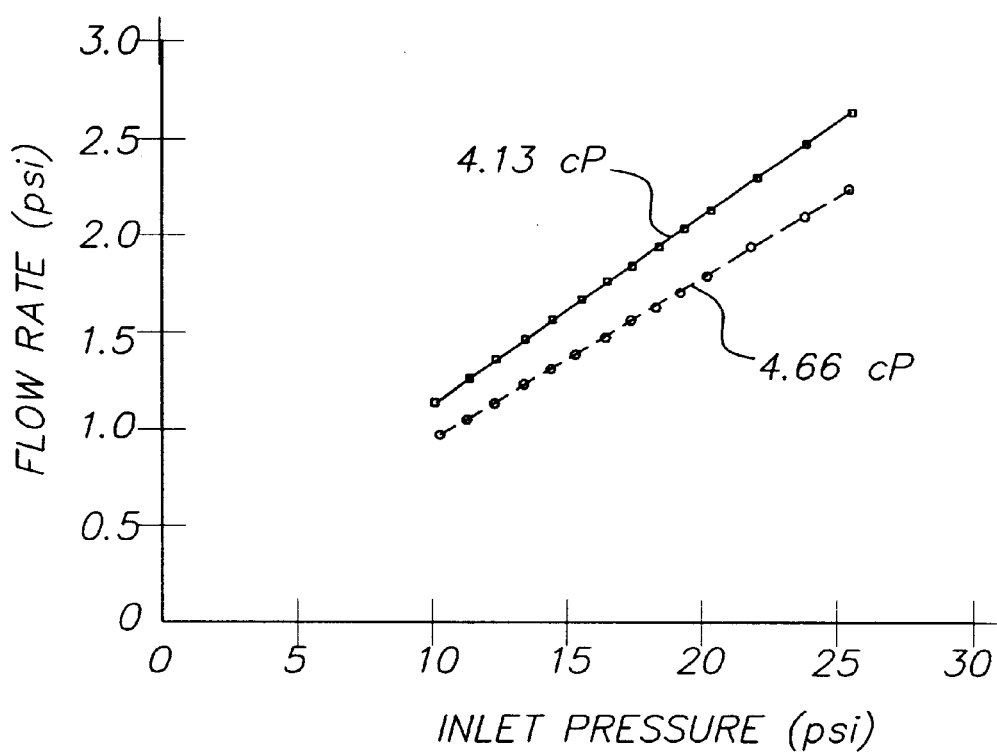
FIG. 5 is a graph of flow rate versus inlet pressure for a porous alumina ceramic restrictor.

FIG. 5 is a graph of flow rate versus driving pressure for 38 and 42% dipropylene glycol methyl ether in water having viscosities of 4.13 and 4.66 cP, respectively. A flow rate difference of 400 ml/s was obtained for a driving pressure of 23 psi. This is twice the differential flow rate measured with the capillary tube restrictor and could be expected to produce a four-fold increase in viscosity resolution. This data was obtained with a 3.8 mm long, 25 mm wide, porous alumina ceramic restrictor having an average pore diameter of 20 $\mu$m, a nominal water filtration specification of 5 $\mu$m and having 40% open area.

The apparatus in accordance with the present invention achieves higher viscosity measurement sensitivity in electing to measure stagnation pressure, which varies as the square of flow rate as opposed to simply measuring the flow rate as described in the prior art. The squared relationship between viscosity and the measured quantity, stagnation pressure, significantly expands the resolution of the new apparatus.

A significant advantage of this viscometer is that it achieves a resolution equal to the best commercial devices at only 1% of their cost. The high resolution is achieved through 1) the selection of a restrictor geometry that maximizes differences in fluid flow rate in response to differences in viscosity and 2) the selection of a measurement parameter that varies as the square of viscosity instead of varying linearly with viscosity. The apparatus can be very compact, use a flow through design to avoid trapping fluid, resists plugging and fouling by avoiding small diameter orifices in the capillary tube embodiment. The apparatus is stable and predictable over a wide range of drive pressures, and introduces no heat energy to the measured fluid.

The invention has been described in detail with particular reference to certain preferred embodiments thereof, but it will be understood that variations and modifications can be effected within the spirit and scope of the invention.

PARTS LIST

| | |
|---|---|
| 10 | apparatus |
| 12 | tubular housing |
| 14 | cavity |
| 14a | cavity portion |
| 16 | fluid restriction device |
| 18 | restrictive tubes |
| 18a | passageways |
| 20 | pressure measuring device |
| 22 | pressure applying device |
| 24 | Pitot tube |
| 26 | Pitot tube |
| 28 | flow area reducer |
| 30 | flow area reducer |

What is claimed is:

1. An apparatus for measuring the viscosity of a Newtonian fluid, comprising:

(a) a tubular housing which defines an internal cavity;

(b) a fluid restriction structure disposed in a first portion of the cavity;

(c) a pressure measuring device disposed to measure the differential pressure in the cavity of the fluid which has flowed through the fluid restriction structure; and (d) a device for applying pressure to the fluid upstream from the fluid restriction structure to cause the fluid to flow through the fluid restriction structure so that the pressure measuring device measures the pressure differential, wherein the viscosity is measured based on the differential pressure being inversely proportional to the fluid viscosity squared.

2. The apparatus of claim 1 wherein the fluid restriction structure includes a plurality of capillary tubes or at least one porous member, which provides circuitous passageways for the fluid.

3. The apparatus of claim 2 wherein the capillary tubes have their internal diameter sized to provide a particular flowrate for the fluid when it has a nominative viscosity.

4. The apparatus of claim 1 wherein the pressure measuring device is a Pitotmeter.

* * * * *